United States Patent [19]
Dorsett et al.

[11] Patent Number: 4,808,518
[45] Date of Patent: Feb. 28, 1989

[54] RECOVERY OF CYTOMEGALOVIRUS ANTIGEN AND USE THEREOF IN AN ASSAY

[75] Inventors: Preston H. Dorsett; Robert F. Naegele, both of Memphis; Terry S. Ratcliffe, Bartlett, all of Tenn.

[73] Assignee: University of Tennessee Research Corporation, Knoxville, Tenn.

[21] Appl. No.: 700,806

[22] Filed: Feb. 11, 1985

[51] Int. Cl.$^4$ ............... G01N 33/543; G01N 133/546
[52] U.S. Cl. ........................................ 435/5; 435/7; 435/810; 435/238; 435/259; 427/2; 436/518; 436/534; 436/543; 436/531; 436/808; 436/811
[58] Field of Search ............... 436/531, 518, 534, 543, 436/808, 811; 435/5, 7, 238, 259, 810; 427/2

[56] References Cited

U.S. PATENT DOCUMENTS

| 3,088,875 | 5/1963 | Fisk | 436/534 |
|---|---|---|---|
| 3,770,383 | 11/1973 | Price | 436/534 |
| 4,315,907 | 2/1982 | Fridlender | 436/542 |
| 4,351,761 | 9/1982 | Gaafar | 424/88 |
| 4,362,531 | 12/1982 | de Steenwinkel | 436/534 |
| 4,374,127 | 2/1983 | Larson | 424/89 |
| 4,395,395 | 7/1983 | Tabor | 436/516 |
| 4,497,899 | 2/1985 | Armstrong | 436/534 |
| 4,590,156 | 5/1986 | Dorsett | 436/533 |
| 4,612,281 | 9/1986 | Desmonts | 436/534 |
| 4,617,379 | 10/1986 | Dobkin | 424/85 |

FOREIGN PATENT DOCUMENTS 0044016 4/1979 Japan .................. 436/534

OTHER PUBLICATIONS

Fuccillo Applied Microbiology 21(1), pp. 104–107, (1971).
Vasconcelos-Costa, Virology 71, pp. 122–133, (1976).
Kettering, J. Clinical Microbiology, 6(6), pp. 647–649, (1977).
Reisfeld, Science 172, pp. 1134–1136, (1971).
Kamiyama, Chemical Abstracts 93:43610m, (1980).
Meltzer, Chemical Abstracts 75:128013x, (1971).

Primary Examiner—Robert J. Warden
Assistant Examiner—Robert Benson
Attorney, Agent, or Firm—Elliot M. Olstein

[57] ABSTRACT

Recovery of antigen from cells containing an intracellular parasite, in particular a virus, by extracting the antigen from the cells with a hypertonic salt solution. CMV antigen extracted in this manner may be supported on particles and used in an agglutination assay for CMV antibody.

19 Claims, No Drawings

RECOVERY OF CYTOMEGALOVIRUS ANTIGEN AND USE THEREOF IN AN ASSAY

This invention relates to the recovery of antigens and to the use thereof, and more particularly to the recovery of antigen from cells. This invention further relates to the preparation of viral antigens supported on a solid support, and an assay employing such viral antigens.

This invention also relates to the recovery of cytomegalovirus (CMV) antigen and the use thereof in an assay for determining CMV antibodies.

Viral antigen has been used in assays for determining the onset of viral infection; in particular, detection of viral antibody in a sample by use of a supported viral antigen.

Procedures have been developed for recovering viral antigens for use in an assay for viral antibody; for example, U.S. Pat. No. 4,195,074 discloses a procedure for recovering soluble ruebella virus antigens; however, such a procedure is complicated.

As a result, there is a need for a simplified procedure for recovering antigens, and in particular, a procedure which can be used for recovering antigens for support on a solid support for use in an assay for antibodies.

In accordance with one aspect of the present invention, there is provided a process for recovering viral antigen, toxoplasmal antigens, chlamydial antigens or mycoplasmal antigens (preferably viral antigens) from cells infected with an intra-cellular parasite which is either virus, toxoplasma, chlamydia or mycoplasma by extracting such antigens from the cells with an aqueous salt solution.

More particularly, the aqueous salt solution is hypertonic with respect to the osmolarity of the cells and is a salt solution which does not adversely affect the immunoreactivity of the extracted antigen. The aqueous salt solution is one which extracts the antigen from the cell without essential destruction of the cells; i.e., the cells remain essentially intact.

The salt may be either an inorganic or an organic salt which is soluble in water, and as representative examples of such salts, there may be mentioned: potassium chloride, guanidine hydrochloride, magnesium chloride, potassium thiocyanate, sodium chloride, etc. Potassuim chloride, magnesium chloride and guanidine hydrochloride are particularity preferred in that the use of such salts results in a higher yield of antigen.

The concentration of salt in the solution is one which provides a hypertonic solution and which effectively extracts the antigen from the cells. In general, the salt concentration is in the order of at least 1.0M and no greater than 5.0M, and preferably at least 2.0M and no greater than 3.5M.

The extraction is accomplished at temperatures which will not denature the antigen. The temperature generally does not exceed about 30° C. The pH of the salt solution is generally maintained at a value so as to maintain stability, with the pH generally being from pH 6 to pH 10. A suitable buffer may be used to maintain the pH.

The cells may be contacted with the salt solution by any one of a wide variety of procedures. Such contacting may be readily accomplished by placing the infected cells in the salt solution and stirring; e.g., with a magnetic stirrer.

After the cells have been contacted for a period of time sufficient to extract the antigen from the cells, the cells are removed from the salt solution; for example, by centrifugation.

The remaining supernatant contains the antigen, and the antigen may be stored for use at a subsequent time, or may be used as hereinafter described.

The salt may be removed from the supernatant, for example, by dialysis of the supernatent against a suitable buffer.

The above procedure is particularly applicable to extracting viral antigen from cells infected with a virus and most particularly to recovering CMV antigen from CMV infected cells. The cells which are infected with CMV are preferably primary human foreskin cells; however, it is to be understood that other cells may be used within the spirit and scope of the invention; for example, human diploid cells other than foreskin cells.

The viral antigens recovered by the present invention, and in particular, CMV antigen, may be supported on a solid support for use in an assay.

In accordance with another aspect of the present invention, it has been found that the viral antigen recovered as hereinabove described should be treated with a detergent prior to being supported on a solid support, particularly in the case where the viral antigen is to be supported on a particulate support for use in an assay for a viral antibody which relies on agglutination of the supported viral antigen.

The viral antigen may be treated with a detergent at a temperature which does not denature the antigen; in particular, a temperature of less than 30° C.

The detergent which is employed for treating the viral antigen, prior to supporting the viral antigen on a solid support, may be any one of a wide variety of surfactants or detergents which do not destroy the antigenic characteristics of the viral antigen, with such detergents being either a cationic, anionic or non-ionic surfactant. Such surfactants are well known in the art, and as representative examples, there may be mentioned alkali metal salts of sulfates, soaps, sulfated or sulfonated oils, various amines, quaternary salts, condensation products with ethylene oxide, etc. Such detergents and surfactants are known in the art. Preferred detergents for such use are alkali (lithium or sodium) dodecyl sulfate, sulfobetain, deoxycholate and laurolylsarcosine, with sodium dodecyl sulfate giving particularly good results.

In general, the surfactant or detergent is employed in a weight ratio of surfactant to virus of from about 0.05 to 1 to about 5 to 1. The selection of an optimum amount is deemed to be within the scope of those skilled in the art from the teachings herein.

After treating the viral antigen with the surfactant or detergent, the viral antigen may be supported on a solid support. The viral antigen is preferably supported on a particulate support; in particular, for use in an assay for an antibody to the virus. The support may be any one of a wide variety of supports, and as representative examples of suitable supports there maybe mentioned synthetic polymer supports, such as polystyrene, polypropylene, substituted polystyrene (e.g., aminated or carboxylated polystyrene), polyacrylamides, polyamides, polyvinylchloride, etc.; glass beads, agarose; cellulose; etc. The supports may be provided with reactive groups; e.g., carboxyl groups, amino groups, etc. to permit direct linking of the virus antigen to the support.

The viral antigen may be supported on the support by a variety of techniques including adsorption; covalent coupling; for example, by activation of the support, or by the use of a suitable coupling agent or by the use of reactive groups on the support. Such procedures are generally known in the art, and no further details are deemed necessary for a complete understanding of the present invention.

The present invention has particular applicability to supporting the viral antigen on a particulate support; however, it is to be understood that the viral antigen could be supported on supports in other forms, such as a test tube, sheet form, etc.

In accordance with a particularly preferred embodiment, the viral antigen which is recovered by the procedure of the present invention, and subsequently treated with a detergent or surfactant, is supported on a particulate support by an adsorption technique, although other techniques may be used. In accordance with the preferred embodiment, the particulate support is a polymer latex, such as polystyrene or polyvinylchloride.

The present invention will be further described with respect to recovering CMV antigen and supporting such recovered CMV antigen on a particulate support for use in an assay for CMV antibody.

In accordance with such a preferred embodiment, the CMV antigen is recovered from cells infected with CMV, with such cells preferably being human foreskin cells. The recovery is effected as hereinabove described by use of an aqueous salt solution, preferably aqueous potassium chloride. The recovered extracted CMV antigen is treated with a detergent or surfactant as hereinabove described, with the surfactant preferably being SDS (sodium dodecyl sulfate). After treatment with the detergent, the CMV antigen is supported on a particulate support, such as polystyrene latex. The particles are provided with an amount of CMV antigen which is effective for an agglutination assay for CMV antibody. Excessive amounts should be avoided in that this may result in bridging of the antibody to be assayed to a single particle. In general, the weight ratio of CMV antigen to support is from 1:10 to 1:500. The selection of an optimum amount is deemed to be within the scope of those skilled in the art from the teachings herein.

In accordance with one technique, after the antigen is adsorbed on the particles, the support, including the adsorbed CMV antigen, is further coated with protein which does not adversely affect the subsequent immunochemical reaction in order to provide a protein coating on the portion of the support which does not include the antigen. The selection of a suitable protein to saturate the spaces between the CMV antigen on the support is deemed to be within the scope of those skilled in the art from the teachings herein. Bovine serum albumin has been found to provide particularly good results.

The CMV antigen sensitized particles, prepared as hereinabove described, are suitable for use in a reagent kit and assay for CMV antibody by a direct agglutination procedure. The reagent kit may include, in addition to the particles sensitized with CMV antigen, in suitable reagent containers, a reactive serum control (contains CVM antibody) and a non-reactive serum control (no CMV antibody); suitable buffers, etc. In accordance with a preferred embodiment, in addition to the reagents, there is provided a test card on which the assay may be effected. The test card has a flat testing surface which includes suitably marked areas (for example, a test circle or more than one test circle) for receiving one or more samples to be assayed, as well as suitably marked areas for each of the serum controls. The test card and the reagents may be included in a single reagent or kit package.

In the agglutination assay, undiluted serum or diluted serum is contacted with the particles which have been sensitized with the CMV antigen, and which have been prepared as hereinabove described, with the presence of CMV antibody being evidenced by visable agglutination.

The assay may be effected quantitiatively by serial diluting the sample, as appropriate, and adding to each serial dilution the CMV antigen sensitized particles. The quantity of antibody in the sample is determined from the highest dilution given any agglutination of the sensitized particle.

The invention will be further described with respect to the following example; however, the scop of the invention is not to be limited thereby;

EXAMPLE

Primary human foreskin cells are infected with AD 169 CMV and incubated for 7 to 10 days at 37° C., followed by harvesting of the infected cells. The cells are scraped into phosphate buffered saline (PBS), and the cells are collected by centrifugation followed by resuspending of the cells in 3M KCL in 0.1M glycine-NaOH buffer, pH. 7.5. The mixture is maintained at 4° C. for 24 hours, with gentle mixing, to extract CMV antigen from the infected cells. After such period, the cells are removed by centrifugation and the supernatant is dialyzed against 1000 volumes of 0.1M Glycine. NaOH pH 7.5. The CMV antigen may be stored by freezing at $-70°$ C.

After determining the protein content from the optical density at 260 mm and 280 mm, the CMV antigen is treated with SDS (0.25 mg SDS per mg of CMV antigen).

Commercial suspensions of polystyrene latex (0.9 micron diameter particles) are washed with carbonate buffer and then resuspended in the carbonate buffer to provide 3% solids (volume to volume).

The hereinabove treated CMV antigen is added to the 3% latex suspension and incubated at 4° C. overnight with tumbling.

The latex is washed with phosphate buffered saline and then resuspended in a phosphate buffered saline solution to which has been added 1% (W/V) bovine serum albumin and 0.1% (V/V) polyoxyethylene sorbitan monolaurate surface active agent (Tween 20) and 0.02% gentamicin. The sensitized latex is allowed to cure for 24 hrs. at 4 degrees C. with gentle stirring.

The sensitized latex may be employed in a test for CMV antibody by use of a test card which includes a marked circle for a reactive control, a marked circle for a non-active control, as well as one or more test samples circles.

25 ul of undiluted serum sample is placed in an appropriate marked serum sample circle, and 25 ul of the reactive and unreactive controls are placed in their respective circles.

With a micropipettor, there is added the sensitized latex (approximately 15 ul), prepared as hereinabove described, followed by rotation on a rotator, and gentle hand rotation.

The card is read microscopically in the wet state under a high intensity incandescent lamp while rotating gently by hand.

The reactive control should show definite agglutination and the non-reactive should show no agglutination.

Any serum sample showing any agglutination should be reported as reactive.

Although the invention has been previously described with respect to CMV antigen, and an assay employing supported CMV antigen for determining CMV antibody, it is to be understood that the teachings are also applicable to recovering other antigens, including, but not limited to: other herpesviruses, such as varicella-zoster, Epstein-Barr (Infectious Mononucleosis); measles virus (rubeola), etc.

Similarly, although the invention has been particularly described with respect to the use of the CMV antigen on a particulate support and an agglutination type of assay, the teachings of the present invention are also applicable to assays other than an agglutination type of assay. Thus, for example, the CMV antigen, or other viral antigen, may be used in an assay wherein, for example, the antibody to CMV virus is determined by a competition type of assay wherein the CMV antigen serves as a binder, and the CMV antibody and a labelled form of the CMV antibody compete for the binding sites on the CMV antigen. Thus, CMV antigen may be supported on a solid support other than a particulate support.

Similarly the invention is applicable to recovering antigens from cells containing antigens from intra-cellular parasites other than viruses, such as toxoplasma, chlamydia, mycoplasma, etc. and to supporting such antigens on a support; and in particular, a particulate support.

The above modifications and others should be apparent to those skilled in the art from the teachings herein.

The extraction procedure herein described is particularly advantageous in that it is relatively simple and does not require purification. Moreover, the cells remain essentially intact whereby it is possible to extract essentially only the desired antigen; in particular, the extraction recovers from virus infected cells predominatly the viral antigen. The assay and in particular the agglutination assay is advantageous in that it is simple and does not require radioactive substances.

The present invention is also advantageous in that it is possible to support the antigen, in particular CMV antigen, assays other than an agglutination type of assay. Thus, for example, the CMV antigen, or other viral antigen, may be used in an assay wherein, for example, the antibody to CMV virus is determined by a competition type of assay wherein the CMV antigen serves as a binder, and the CMV antibody and a labelled form of the CMV antibody compete for the binding sites on the CMV antigen. Thus, CMV antigen may be supported on a solid support other than a particulate support.

Similarly the invention is applicable to recovering antigens from cells containing antigens from intra-cellular parasites other than viruses, such as toxoplasma, chlamydia, microplasma, etc. and to supporting such antigens on a support; and in particular, a particulate support.

The above modifications and others should be apparent to those skilled in the art from the teachings herein.

The extraction procedure herein described is particularly advantageous in that it is relatively simple and does not require purification. Moreover, the cells remain essentially intact whereby it is possible to extract essentially only the desired antigen; in particular, the extraction recovers from virus infected cells predominatly the viral antigen. The assay and in particular the agglutination assay is advantageous in that it is simple and does not require radioactive substances.

The present invention is also advantageous in that it is possible to support the antigen, in particular CMV antigen, on a particulate support wherein the antigen sensitized particles are resistant to self agglutination; in particular where the antigen is supported on latex particles for use in an agglutination type of assay. These and other advantages should be apparent to those skilled in the art from the teachings herein.

Numerous modifications and variations of the present invention are possible in light of the above teachings and, therefore, within the scope of the appended claims, the invention may be practiced otherwise than as particularly described.

What is claimed is:

1. A composition for use in an agglutination assay for detection of CMV antibody, comprising:
   solid particles sensitized with CMV antigen, said CMV antigen having been obtained by extracting the CMV antigen from cells containing CMV antigen with an aqueous salt solution hypertonic with respect to the osmolarity of the cells.

2. The composition of claim 1 wherein said antigen was treated with a detergent prior to sensitizing the solid particles.

3. The composition of claim 2 wherein the particulate support is a synthetic polymer.

4. The composition of claim 3 wherein the polymer is polysyrene.

5. The composition of claim 4 wherein the antigen is adsorbed on the particulate support.

6. A process for assaying a sample for CMV antibody, comprising: adding to the sample the particulate support sensitized with CMV antigen of claim 1; and determining agglutination of sensitized particles.

7. A process for assaying a sample for CMV antibody, comprising: adding to the sample the particulate support sensitized with CMV antigen of claim 2; and determining agglutination of sensitized particles.

8. A process for producing a particulate support sensitized with CMV antigen, comprising:
   contacting cells containing CMV antigen with an aqueous salt solution hypertonic with respect to the osmolarity of the cells to extract CMV antigen from the cells; treating extracted CMV antigen with a detergent; and supporting treated CMV antigen on a solid particulate support.

9. The process of claim 8 wherein the antigen is supported on the support by adsorption.

10. The process of claim 9 wherein the salt is selected from the group consisting of potassium chloride, magnesium chloride and guanidine hydrochloride.

11. The process of claim 9 wherein the particulate support is a synthetic polymer.

12. The process of claim 11 wherein the particulate support is polystyrene, the salt is potassium chloride and the detergent is an alkali dodecyl sulfate.

13. The process of claim 11 wherein the polymer is polystyrene.

14. A process for assaying a sample for CMV antibody, comprising: adding to the sample a particulate support sensitized with CMV antigen prepared by the process of claim 9; and determining agglutination of sensitized particles.

15. A process for assaying a sample for CMV antibody, comprising: adding to the sample a particulate support sensitized with CMV antigen prepared by the process of claim 13; and determining agglutination of sensitized particles.

16. A process for assaying a sample for CMV antibody, comprising: adding to the sample a particulate support sensitized with CMV antigen prepared by the process of claim 11; and determining agglutination of sensitized particles.

17. A process for assaying a sample for CMV antibody, comprising: adding to the sample a particulate support sensitized with CMV antigen prepared by the process of claim 12; and determining agglutination of sensitized particles.

18. An assay kit for determining CMV antibody, comprising:
said kit comprising a reagent container containing solid particles sensitized with CMV antigen prepared by the process of claim 12.

19. The kit of claim 18 wherein said kit further includes a test card having a flat surface for receiving an assay sample and the sensitized particles.

* * * * *